United States Patent [19]

Miyazaki

[11] Patent Number: 5,507,187
[45] Date of Patent: Apr. 16, 1996

[54] WHEEL-ACTING FORCE MEASURING DEVICE

[75] Inventor: Nagao Miyazaki, Osaka, Japan

[73] Assignee: Japan Electronics Industry, Limited, Osaka, Japan

[21] Appl. No.: 195,418

[22] Filed: Feb. 14, 1994

[30] Foreign Application Priority Data

Feb. 15, 1993 [JP] Japan .................. 5-065891

[51] Int. Cl.⁶ .................................. G01L 5/16
[52] U.S. Cl. .................. 73/769; 73/862.046; 73/146; 73/118.1
[58] Field of Search ............... 73/769, 768, 763, 73/11.01–11.09, 146, 118.1, 770, 862.338, 862.474, 862.627, 862.041–862.046

[56] References Cited

U.S. PATENT DOCUMENTS

| | | | |
|---|---|---|---|
| 3,350,926 | 11/1967 | Webb | 73/768 |
| 3,620,074 | 11/1971 | Laimins et al. | 73/862.66 |
| 4,059,991 | 11/1977 | Dybel et al. | 73/769 |
| 4,138,882 | 2/1979 | Lockery et al. | 73/769 |
| 4,576,053 | 3/1986 | Hatamura | 73/862.66 |
| 4,621,533 | 11/1986 | Gindy . | |
| 4,748,844 | 6/1988 | Yoskikawa et al. | 73/862.044 |
| 4,936,149 | 6/1990 | Jacobson | 73/768 |
| 4,977,784 | 12/1990 | Eckerle | 73/862.041 |

FOREIGN PATENT DOCUMENTS

| | | |
|---|---|---|
| 0504731 | 9/1992 | European Pat. Off. . |
| 2389878 | 12/1978 | France . |
| 63-138228 | 6/1988 | Japan ........ 73/862.627 |
| 63-300928 | 12/1988 | Japan ........ 73/862.627 |
| 2138840 | 5/1990 | Japan ........ 73/862.627 |
| 4331336 | 11/1992 | Japan . |
| 972274 | 11/1982 | U.S.S.R. . |
| 1769013 | 10/1992 | U.S.S.R. . |
| 2184996 | 7/1987 | United Kingdom . |

OTHER PUBLICATIONS

"Antilock Brake System (M–ABS) Based on the Friction Coefficient Between the Wheel and the Road Surface" by N. Miyasaki et al, SAE Technical Paper Series, International Congress and Exposition, Detroit, Michigan Feb. 26–Mar. 2, 1990.

*Primary Examiner*—Richard Chilcot
*Assistant Examiner*—Jewel V. Artis
*Attorney, Agent, or Firm*—Jordan and Hamburg

[57] ABSTRACT

A wheel-acting force measuring device permits accurate measurement of a shearing stress by removing a torsional stress component measured by a stress detector. A stress sensor includes four sensor segments which measure stress by a change in a characteristic thereof, arranged two on each of opposed surfaces of a base, preferably in cross form. The four sensor segments can be combined into various circuit configurations to produce a combined characteristic for each combination, each associated with a measurement of a particular stress acting on a wheel. In a preferred case, the four sensor segments are strain gauges, each which form part of a bridge circuit shiftably connected to allow the relative connection of each segment to be altered, thereby changing the configuration of the bridge. When in a first configuration, the output of the bridge circuit indicates primarily shearing strain mixed with a torsional strain component. When switched to a second switch position, the output of the bridge circuit indicates torsional stress. The torsional component may then be subtracted from the combined output measured when switched to the first position, yielding a value for the shear stress alone. The above may further be carried out using a logic bridge circuit arrangement to variably combine the segments. In a further embodiment, a plurality of stress sensors may be analyzed as above, the stress determined for each then extrapolated to yield a maximum value of shearing strain.

11 Claims, 9 Drawing Sheets

(CHANGES IN RESISTANCE VALUE OF BRIDGE SEGMENTS)

| | PRE-STRESS-APPLICATION (3-1) | SHEARING STRAIN (3-2) | STRAIN DUE TO BRAKE TORQUE (TORSION) (3-3) |
|---|---|---|---|
| FRONT |  10 |  12 |  14 |
| BACK |  11 | 13 | 15 |

WHEEL-ACTING FORCE MEASURING DEVICE

BACKGROUND OF THE INVENTION

The present invention relates to improvements in Japanese Patent Application No. Hei 3-130840 and more particularly to a wheel-acting force measuring device for measuring forces acting on a wheel, such as a road surface friction force and a road surface friction coefficient, which can be used as a component of either an antilock brake system (ABS) for preventing the locking of wheels on application of the hard brake to the vehicle or a traction control system (TCS) for preventing excessive slippage of wheels during acceleration.

The present applicant has previously proposed, in Japanese Patent Application No. Hei 3-130840, a wheel-acting force measuring device comprising a hole formed in or adjacent an axle, a stress detecting sensor, such as a road surface friction detecting sensor or a road surface friction coefficient detecting sensor, fixedly embedded in said hole directly or through a spacing agent such that said stress detecting sensor is disposed on the stress center axis, the detection signal from said stress detecting sensor being processed in a signal processing circuit composed of a bridge circuit.

With the wheel-acting force measuring device described above, the complicated structure of the axle and vehicle body sometimes causes the stress detecting sensor and sensor segment to deviate from the ideal positions on the stress center axis of the brake torque, resulting in the brake torque (torsional torque) component, in addition to the shearing stress, being mixed in the bridge output of the signal processing circuit.

Therefore, in such case, the correct stresses, such as the road surface friction force and road surface friction coefficient, cannot be detected and hence an antilock brake device or traction control system of high precision cannot be obtained. Thus, it is necessary to eliminate cross talk due to brake torque.

SUMMARY OF THE INVENTION

The present invention has been accomplished with the above in mind and is intended to automatically remove the brake torque component mixed in the stress detecting sensor output when stresses in the wheel are to be detected.

In a first embodiment, the present invention provides a device for measuring stresses acting on the wheel, and more particularly a shearing stress detecting device, comprising a stress detecting sensor having four sensor segments in the form of strain gauges attached to the front and back of a thin base sheet, said stress detecting sensor being installed on the stress center line of or adjacent an axle of a vehicle, said stress detecting sensor being constructed in the form of a bridge circuit whose sensor segments are adapted to be shiftily connected, the arrangement being such that after the brake torque component mixed in the shearing stress detecting device has been found, it is removed from the shearing stress detecting device by using said brake torque component as correction term.

In this device, the connection of the sensor segments of the stress detecting sensor can be optionally changed to provide a setting adapted to preferentially selectively detect a desired stress, thus eliminating the brake torque component mixed in the shearing stress detecting device.

The present invention further provides in a second embodiment a shearing stress detecting device, comprising a stress detecting sensor having four sensor segments in the form of strain gauges attached to the front and back of a thin base sheet, said stress detecting sensor being installed on the stress center line of or adjacent an axle of a vehicle, said stress detecting sensor being constructed in the form of a bridge circuit whose sensor segments are adapted to be shiftily connected, so that the side force can be detected by shifting it downward through 90 degrees (F-direction).

In the above embodiment of the wheel-acting force measuring device, the side stress can be detected by changing the connection of the sensor segments of the stress detecting sensor through 90 degrees, i.e., in the F-direction.

A third embodiment of the invention still further provides a device for measuring stresses acting on a wheel as set forth in the first embodiment described above, wherein the four sensor segments a, b, c, d in the form of strain gauges of the stress detecting sensor are logically constructed to form four bridge circuits, the output from each bridge circuit being fed into an arithmetic circuit for finding the value of $b/(a+b)-c/(c+d)=A$ (shearing strain equivalent) and an arithmetic circuit for finding the value of $b/(a+b)-d/(c+d)=B$ (brake torque component equivalent), the outputs from the two arithmetic circuits being fed into an arithmetic circuit for finding the value of $A-\alpha B=C$ (shearing strain with brake torque component removed) so as to remove the brake torque component mixed in the shearing stress detecting device.

In the above wheel-acting force measuring device, the four bridge circuits logically constructed of four sensor segments forming the stress detecting sensor each detect the the shearing strain equivalent and the brake torque component equivalent, the outputs being calculated in the arithmetic circuits for finding these values, the output from the two arithmetic circuits being fed into the arithmetic circuit which subtracts the value of the brake torque component equivalent from the value of the shearing strain equivalent, this operation resulting in the brake torque component being removed in the logic block.

The invention yet further provides in a fourth embodiment a device for measuring stresses acting on a wheel as set forth in the first and third embodiments described above, wherein a stress detecting sensor body comprising a plurality of stress detecting sensors in the form of strain gauges attached to a common base sheet at suitable intervals is installed on the stress center axis of or adjacent the axle of a vehicle to form a shearing stress detecting device, the four sensor segments in the form of strain gauges of each stress detecting sensor of said stress detecting sensor body are logically constructed to form four bridge circuits so as to constitute a plurality of logic circuits corresponding to the number of the stress detecting sensors, the output from the arithmetic circuit of each logic circuit for finding the value of the shearing strain equivalent A and the output from the arithmetic circuit of each logic circuit for finding the value of brake torque component equivalent B are fed into a tendency deciding arithmetic circuit for the value of shearing strain equivalent and a tendency deciding arithmetic circuit for the value of brake torque component equivalent, the outputs from the two tendency deciding arithmetic circuits being fed into a comparison arithmetic circuit, thereby removing the brake torque component mixed in the shearing stress detecting device.

In the above wheel-acting force measuring device, the shearing strain equivalent and the brake torque component equivalent are detected in a plurality of logic circuits corresponding to a plurality of stress detecting sensors attached to a single base sheet, the outputs from the logic circuits are fed into the tendency deciding arithmetic circuit for the value of shearing strain equivalent and the tendency deciding arithmetic circuit for the value of brake torque component equivalent, the tendencies are selected by arithmetic operations from the values of a plurality of shearing strain equivalents and the values of a plurality of brake torque component equivalents in said two tendency deciding arithmetic circuits, the selected outputs are fed into a comparison circuit, the brake torque component equivalents are removed from the shearing strain equivalents by arithmetic operations, and the stress detecting sensor located in the optimum position is automatically selected from the plurality of stress detecting sensors, so that the brake torque component mixed in the shearing stress detecting device is eliminated in the logic block.

DESCRIPTION OF THE PREFERRED EMBODIMENT

Embodiment of the invention will now be described with reference to the drawings. Herein shown are examples of preferred embodiments and the scope of the invention is not limited thereto.

Figure 1:
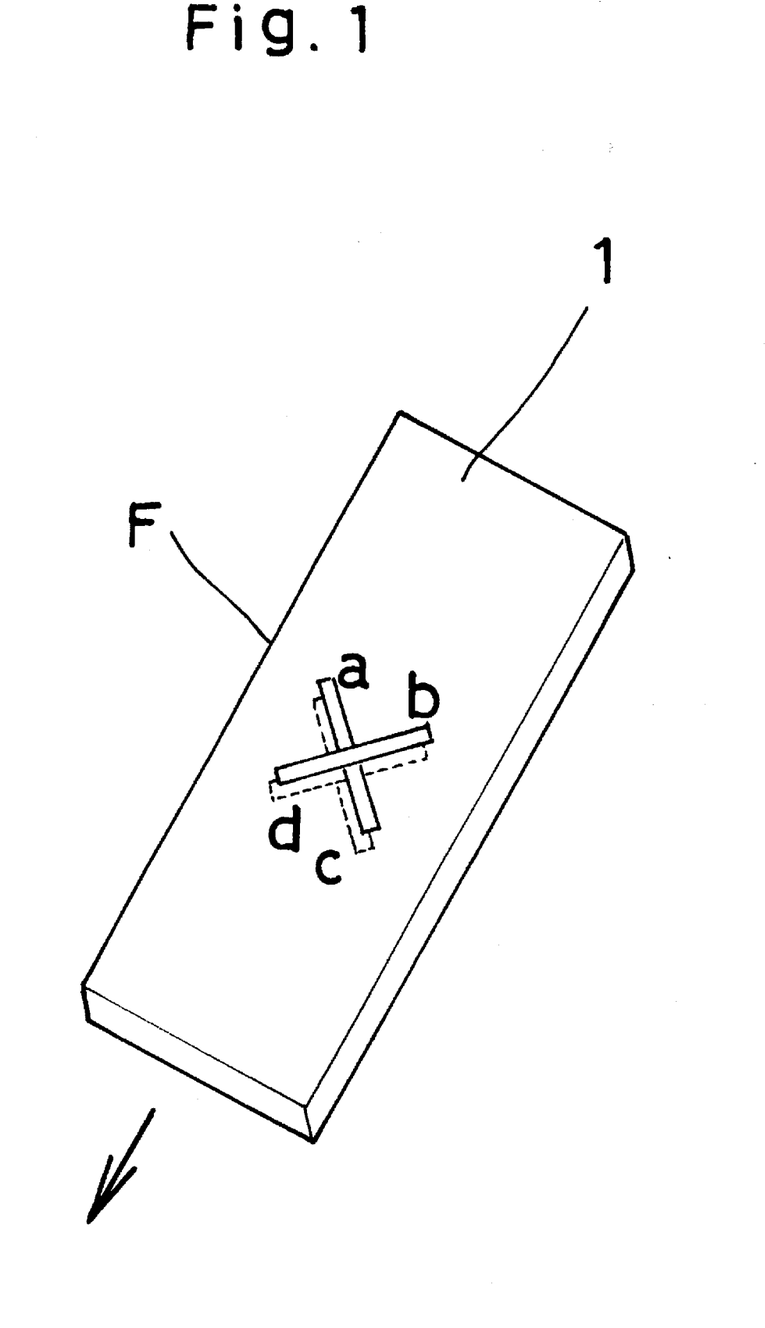
FIG. 1 is a perspective view of a stress detecting sensor used in a wheel-acting force measuring device according to the present invention.

FIG. 1 is a perspective view showing an example of a stress detecting sensor according to the present invention. This stress detecting sensor F comprises four strain gauges a, b, c, d of metal resistance wire bonded, in twos each in cross form, to the front and back of a thin base sheet 1 of plastic material, such as epoxy resin, metal, silicone or the like, said base sheet being installed directly on the stress center axis of or adjacent an axle for a nondriven wheel of an automobile having a strut type suspension construction or being embedded in a hole, so as to detect stresses acting on a wheel, such as the road surface friction force and road surface friction coefficient.

Figure 2:
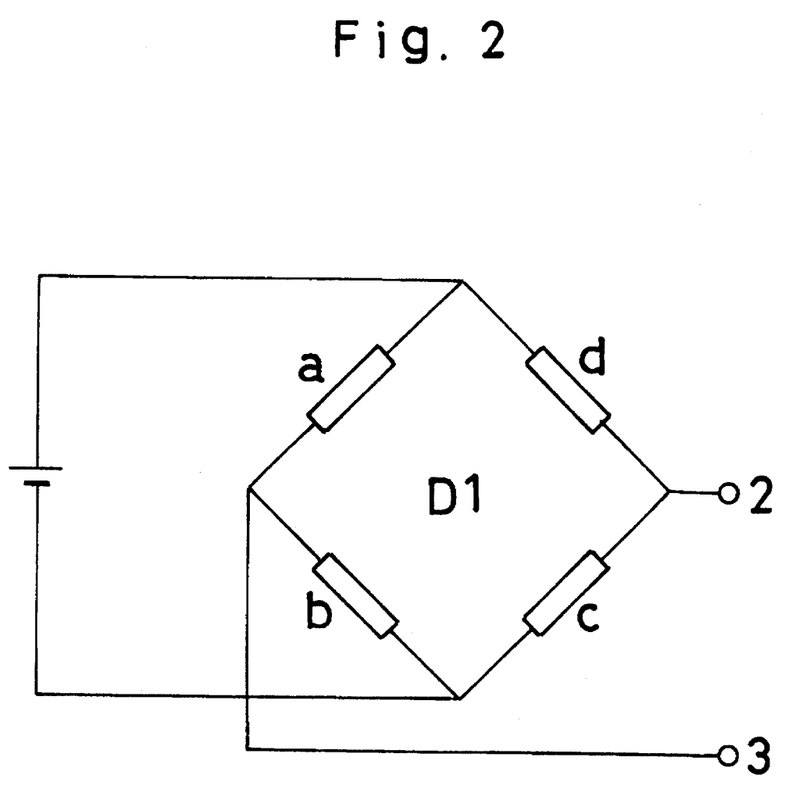
FIG. 2 is a diagram of a bridge circuit of the sensor segments of stress detecting sensor
Figure 3:
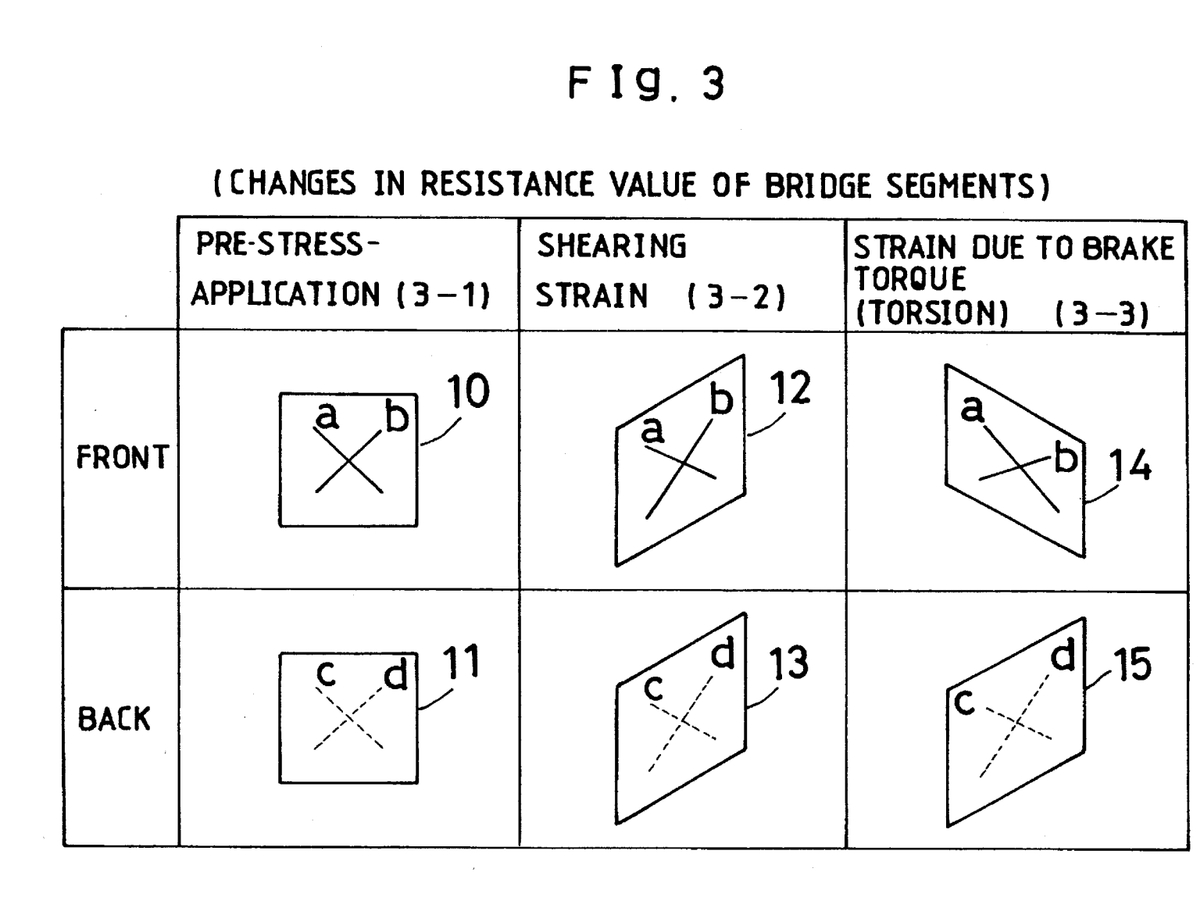
FIG. 3 is an explanatory view showing changes in the resistance value of the sensor segments of a bridge circuit shown in FIG. 2.

In the case where stresses are to be detected, the four strain gauges a, b, c, d are connected to form a bridge circuit D1, as shown in FIG. 2, so that a stress is derived in the form of a signal from the output terminals 2 and 3. When a strain is produced in the thin base sheet 1 of the stress detecting sensor F, the four sensor segments a, b, c, d (strain gauges) disposed on the front and back thereof changes such that if the direction of travel of the vehicle is as shown by the arrow in FIG. 1, the pre-stress-application state (3-1) with 10 and 11 for the front and back in FIG. 3 changes, in the case of a shearing strain, to the post-stress-application state (3-2) with 12 and 13 for the front and back whose changes are substantially the same. On the other hand, in the case of a strain produced by brake torque, since the sensor segments a, b, c, d are disposed in a symmetrical position with respect to the stress center axis, a torsional strain is produced in the thin base sheet 1, so that changes are opposite in pushing and equal in size, as shown at 14 and 15 in the state (3—3) in FIG. 3.

Therefore, in the case of the bridge structure shown in FIG. 2, for a shearing stress, the output is obtained from the relations a=c and b=d, and for a brake torque (torsional torque) the output is zero from the relations a=c and b=d; thus, the bridge circuit delivers its output only for a shearing stress. However, this case where said brake torque (torsional torque) results in zero output takes place only when said stress detecting sensor F is disposed ideally in alignment with the stress center axis. In practice, because of the structure of the vehicle, it is extremely difficult from the standpoint of the technique of attaching said stress detecting sensor to dispose the stress detecting sensor in exact alignment with the stress center axis of or adjacent the axle. In many cases, such stress detecting sensor is disposed more or less deviated from the stress center axis, resulting in the brake torque (torsional torque) component being contained in the output from the circuit. If the bridge circuit is constructed by interchanging the sensor segments (strain gauges) d and c as shown in FIG. 4, then for a shearing stress, a=c and b=d with zero output, and for a brake torque (torsional torque), a≠c and b≠d, so that the brake torque component can be detected.

Figure 4:
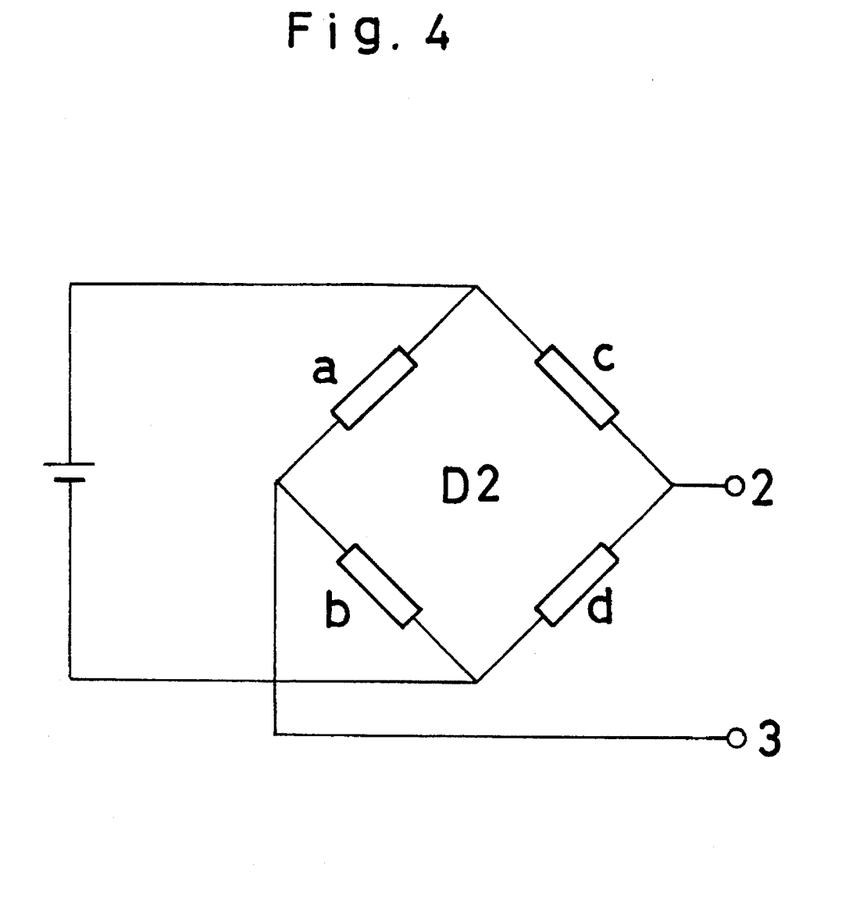
FIG. 4 is a diagram of a circuit diagram having a different relation of connection of the sensor segments.
Figure 5:
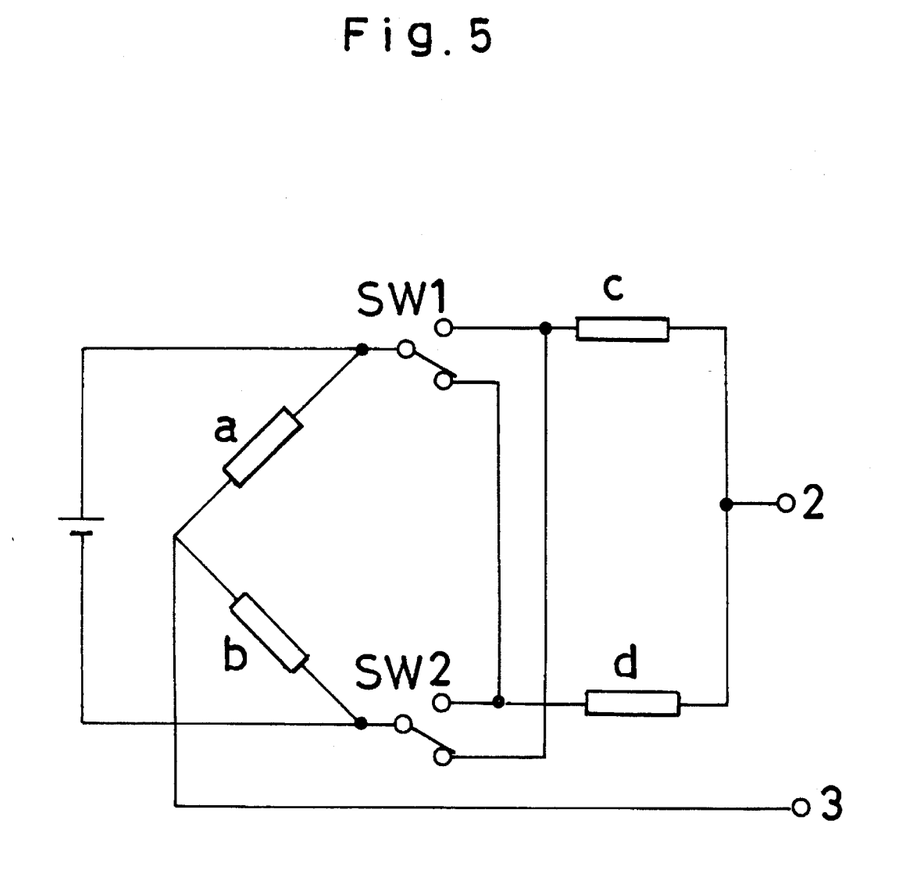
FIG. 5 is a diagram of a bridge circuit capable of changing the connection of the sensor segments.

Thus, by shiftily connecting the bridge circuit D1 shown in FIG. 2 and the bridge circuit D2 shown in FIG. 4 by means of mode change switches SW 1 and SW2 as shown in FIG. 5, two types of quantities can be detected using a single bridge circuit; more particularly, a stress with a brake torque component mixed therein as in the bridge circuit D1 shown in FIG. 2 can be detected and by changing the mode change switches, a brake torque component alone as in the bridge circuit D2 shown in FIG. 4 can be detected. Thus, the shearing stress without brake torque component can be obtained by subtracting the detected value of the brake torque alone from the detected value of the stress having brake torque component mixed therein.

Figure 6:
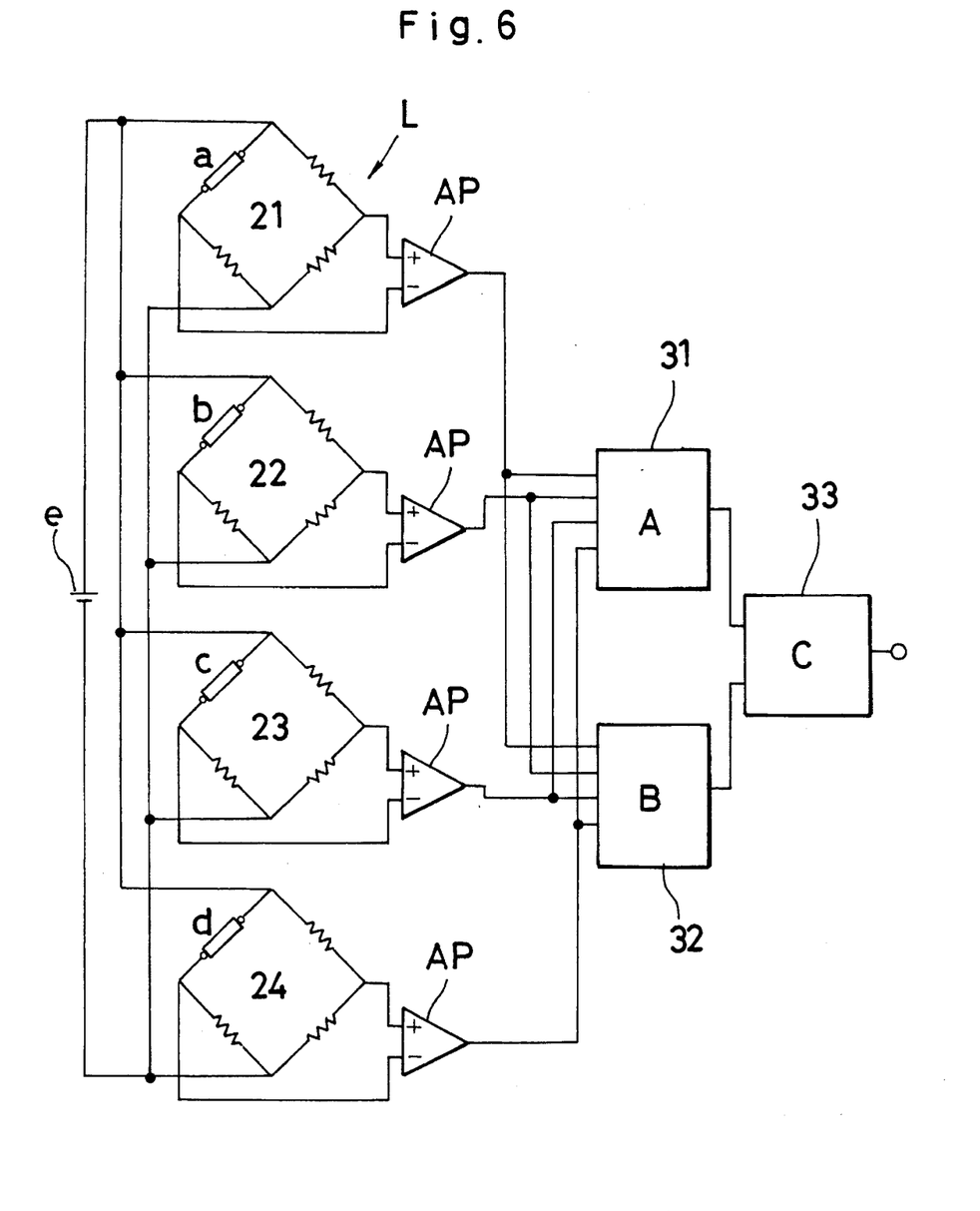
FIG. 6 is a block diagram showing an example of the hardware construction of a wheel-acting force measuring device described in Claim 3.

FIG. 6 shows a further embodiment of the invention as wherein shift connection of the bridge circuits D1 and D2 is constructed in a logic bridge manner. In this embodiment, four sensor segments a, b, c, d constitute independent bridge circuits 21, 22, 23, 24 which are connected to a common power source e. the output terminals of the bridge circuits are connected to arithmetic circuits 31 and 32 through amplifiers AP, thereby forming a logic bridge L. The arithmetic circuit 31 is used to find the value of the same arithmetic operation as in the bridge circuit D1 shown in FIG. 2, i.e., the value of $b/(a+b)-c/(c+d)=A$ (shearing strain equivalent) and the arithmetic circuit 32 is used to find the value of the same arithmetic operation as in the bridge circuit D2 shown in FIG. 4, i.e., the value of $b/(a+b)-d/(c+d)=B$ (brake torque component equivalent), the outputs from these two arithmetic circuits being fed into the arithmetic circuit 33, where the value of $A-\alpha B=C$ (shearing strain with brake torque component removed) is found, whereby a detection signal with brake torque component removed is obtained. In addition, $\alpha$ is a coefficient which is empirically determined.

Figure 7:
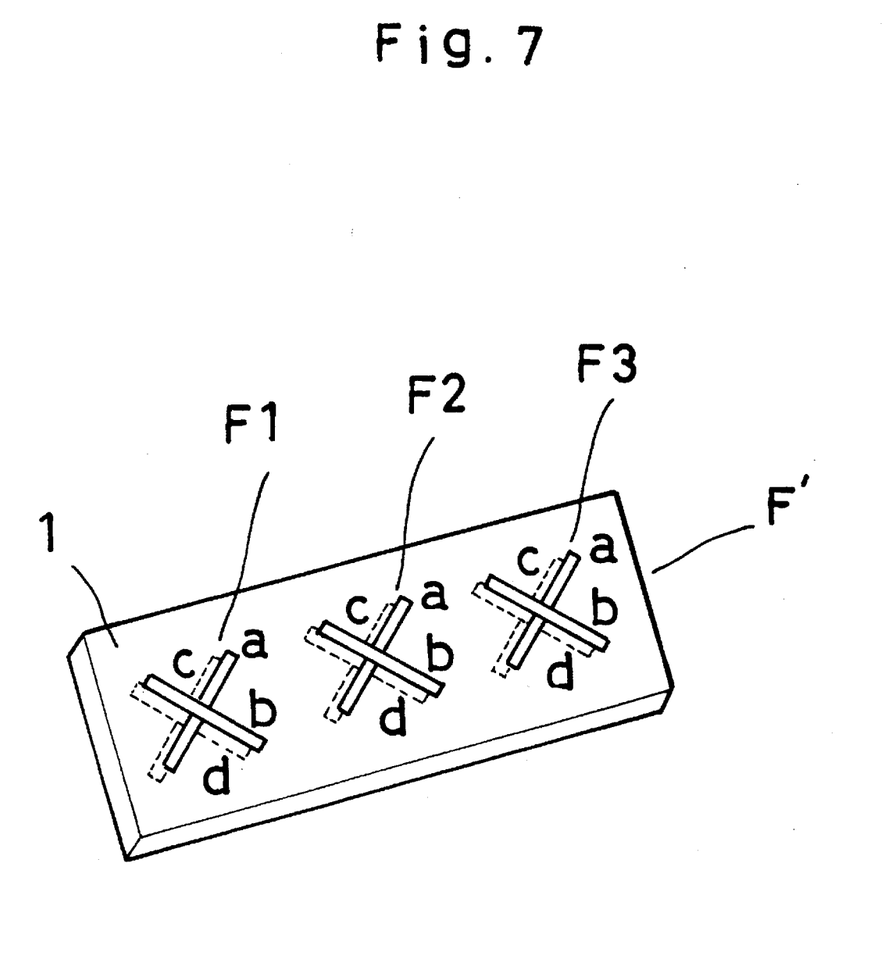
FIG. 7 is a perspective view of a stress detecting sensor body used in a wheel-acting force measuring device described in Claim 4.
Figure 8:
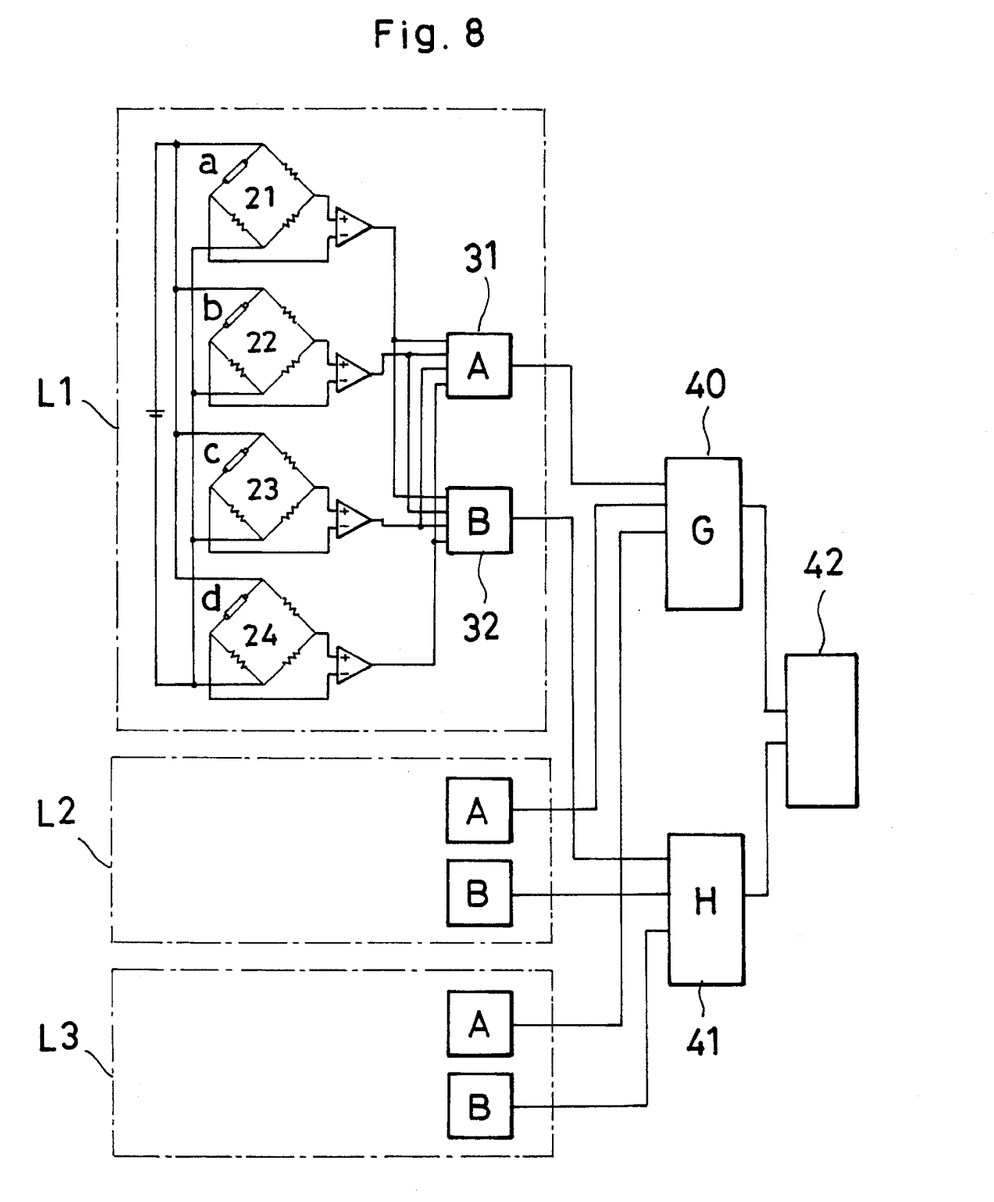
FIG. 8 is a block diagram showing an example of the hardware construction of a wheel-acting force measuring device described in Claim 4.
Figure 9:
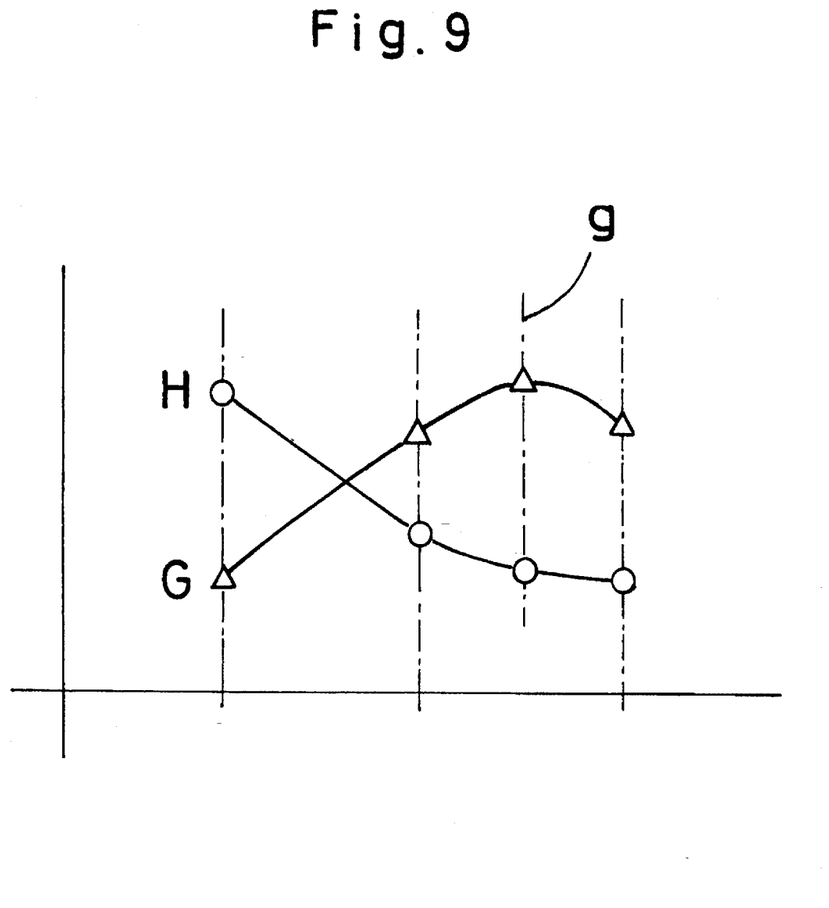
FIG. 9 is an explanatory view for finding an imaginary line representing the stress center axis.

FIG. 7 shows an embodiment of a stress detecting sensor body F' used in the present invention described in Claim 4, comprising stress detecting sensors F1, F2, F3 each of which is the same as the stress detecting sensor F consisting of four strain gauges shown in FIG. 1 and which are integrally disposed with a suitable distance therebetween, said stress detecting sensor body being directly attached to or adjacent an axle or being embedded in a hole formed in or adjacent an axle, said stress detecting sensors F1, F2, F3 being constructed to form logic circuits L1, L2, L3 as shown in FIG. 8, each being the same as that shown in FIG. 6, the outputs from the arithmetic circuits of 31 and 32 of the logic circuits being fed into a tendency deciding arithmetic circuit 40 for the value of shearing strain equivalent and a tendency deciding arithmetic circuit 41 for the value of brake torque component equivalent, thereby reading the tendency of the value A of shearing strain equivalent and the tendency of the value B of brake torque (torsional torque) component equivalent. The outputs from the two tendency deciding arithmetic circuits are fed into an arithmetic circuit 42 for finding an imaginary line (g in FIG. 9) indicating the ratio of the outputs G and H such that the signal component of the output value G of shearing strain equivalent is at a maximum. And by arithmetic operations it is possible to find an imaginary line g indicating the removal of the brake torque component.

According to a feature of the first and second embodiments of the wheel-acting force measuring devices described herein, desired stresses can be obtained by optionally changing the sensor segments of the stress detecting sensor and hence the stress with brake torque component removed can be easily obtained.

The wheel-acting force measuring device according to the aforementioned third embodiment has a particular advantage of being capable of detecting a stress in which the brake torque (torsional torque) component, which cannot be removed by the ordinary bridge arrangement because of the complicated construction of the vehicle and its axles, mixed in the shearing stress detection value, has been removed by arranging the sensor segments of the stress detecting sensor to form a logic bridge.

Further, the wheel-acting force measuring device according to the aforementioned fourth embodiment has a peculiar advantage of being capable of reading the tendencies of the shearing strain equivalent output and brake torque component, automatically selecting the optimum value so as to detect a stress with the brake torque component removed even in the case where because of the construction of the vehicle or axle, a stress detecting sensor cannot be installed on the stress center axis where the brake torque component is at a minimum.

What is claimed is:

1. A wheel-acting force measurement device, which is a shearing stress detecting device, comprising:

a stress detecting sensor having four sensor segments in the form of strain gauges attached to the front and back of a thin base sheet, said stress detecting sensor being installed on the stress center line of or adjacent an axle of a vehicle;

said stress detecting sensor being constructed in the form of a bridge circuit whose sensor segments are to be shiftably connected, the arrangement being such that after the brake torque component mixed in the shearing stress detecting device has been found, it is removed from the shearing stress detecting device by using said brake torque component as correction term, thereby detecting stresses acting on the wheel.

2. A wheel-acting force measurement device, which is a shearing stress detecting device, comprising:

a stress detecting sensor having four sensor segments in the form of strain gauges attached to the front and back of a thin base sheet, said stress detecting sensor being installed on the stress center line of or adjacent an axle of a vehicle;

said stress detecting sensor being constructed in the form of a bridge circuit whose sensor segments are to be shiftably connected, so that the side force can be detected by shifting it downward through 90 degrees.

3. A wheel-acting force measuring device as set forth in claim 1, wherein the four sensor segments a, b, c, d in the form of strain gauges of the stress detecting sensor are logically constructed to form four bridge circuits, the output from each bridge circuit being fed into an arithmetic circuit for finding the value of $b/(a+b)-(c+d)=A$ (shearing strain equivalent) and an arithmetic circuit for finding the value of $b/(a+b)-d/(c+d)=B$ (brake torque component equivalent), the outputs from the two arithmetic circuits being fed into an arithmetic circuit for finding the value of $A-\alpha B=C$ (shearing stress with brake torque component removed) so as to remove the brake torque component mixed in the shearing stress detecting device.

4. A wheel-acting force measuring device as set forth in claim 1 wherein a stress detecting sensor body comprising a plurality of stress detecting sensors in the form of strain gauges attached to a common base sheet at suitable intervals is installed on the stress center axis of or adjacent the axle of a vehicle to form a shearing stress detecting device, the four sensor segments in the form of strain gauges of each stress detecting sensor of said stress detecting sensor body are logically constructed to form four bridge circuits so as to constitute a plurality of logic circuits corresponding to the number of the stress detecting sensors, the output from the arithmetic circuit of each logic circuit for finding the value of the shearing strain equivalent A and the output from the arithmetic circuit of each logic circuit for finding the value of brake torque component equivalent B are fed into a tendency deciding arithmetic circuit for the value of shearing strain equivalent and a tendency deciding arithmetic circuit for the value of brake torque component equivalent, the outputs from the two tendency deciding arithmetic circuits being fed into a comparison arithmetic circuit, thereby removing the brake torque component mixed in the shearing stress detecting device.

5. A device for measuring stresses acting on a wheel, said device comprising:

a stress detecting sensor including a base having two sides;

said stress detecting sensor including four sensor segments attached to said base and arranged two on each of the two sides of said base;

each of said four sensor segments including means responsive to a deformation thereof to produce a change in an individual characteristic of each said sensor segment;

means for shiftably connecting said four sensor segments into a plurality of combinations to produce a combined characteristic for each of said plurality of combinations, each of said combined characteristics being dependent upon each of said individual characteristic and upon a relative positioning of each of said four sensor segments; and each of said plurality of combinations being associated with a measurement of a particular one of said stresses acting on said wheel.

6. The wheel-acting shearing stress measuring device according to claim 5, wherein:

said sensor segments are strain gauges; and said characteristic is electrical resistance.

7. The wheel-acting shearing stress measuring device according to claim 5, wherein said means for shiftably connecting said four sensor segments into a plurality of combinations includes switchably arranging said segments to form a bridge circuit having one of a plurality of configurations for producing a plurality of selectable outputs each representing measurement of a particular stress corresponding to a respective one of said plurality of configurations.

8. The wheel-acting shearing stress measuring device according to claim 5, wherein said means for shiftably connecting said four sensor segments into a plurality of combinations includes;

a plurality of individual bridges, each including one of said four sensors to produce outputs therefrom; and first and second arithmetic circuits including means for performing a particular arithmetic operation on said outputs fed therein to produce a combined shearing stress value and a torsional stress value respectively therefrom.

9. The wheel-acting shearing stress measuring device according to claim 8, further comprising a third arithmetic circuit including means for subtracting said torsional stress value, adjusted by a coefficient, from said combined shearing stress value whereby a filtered value of shearing stress may be determined.

10. A wheel-acting shearing stress measuring device, comprising:

a stress detecting sensor including a base having two sides;

said stress detecting sensor including four sensor segments in the form of strain gauges attached to said base and arranged two on each of said two sides of said base; and means for shiftably interconnecting each of said sensor segments to form a bridge circuit having one of a plurality of configurations, a plurality of selectable outputs of said bridge circuit each representing measurement of a particular stress corresponding to a respective one of said plurality of configurations.

11. The wheel-acting shearing stress measuring device according to claim 10, further comprising:

a first configuration of said plurality of configurations in which a first output from said bridge circuit represents a measured shearing stress;

said first output including a torsional stress component when said stress detecting sensor is misaligned with a stress center axis;

a second configuration in which a second output from said bridge circuit represents a measured torsional stress; and means for removing said component of torsional stress from said first output by subtracting an empirically adjusted value of said second output.

* * * * *